(12) United States Patent
Bebernitz

(10) Patent No.: US 7,812,167 B2
(45) Date of Patent: *Oct. 12, 2010

(54) SUBSTITUTED (THIAZOL-2-YL)-AMIDES OR SULFONAMIDES AS GLUCOKINASE ACTIVATORS USEFUL IN THE TREATMENT OF TYPE 2 DIABETES

(75) Inventor: Gregory Raymond Bebernitz, Stow, MA (US)

(73) Assignee: Novartis, AG, Basel (CH)

( * ) Notice: Subject to any disclaimer, the term of this patent is extended or adjusted under 35 U.S.C. 154(b) by 1316 days.

This patent is subject to a terminal disclaimer.

(21) Appl. No.: 10/529,670

(22) PCT Filed: Oct. 2, 2003

(86) PCT No.: PCT/EP03/10977

§ 371 (c)(1),
(2), (4) Date: Aug. 15, 2005

(87) PCT Pub. No.: WO2004/050645

PCT Pub. Date: Jun. 17, 2004

(65) Prior Publication Data

US 2005/0282851 A1 Dec. 22, 2005

Related U.S. Application Data

(60) Provisional application No. 60/415,860, filed on Oct. 3, 2002.

(51) Int. Cl.
*A61K 31/426* (2006.01)
*A61K 31/429* (2006.01)
*C07D 277/46* (2006.01)
*C07D 277/52* (2006.01)
*C07D 513/02* (2006.01)

(52) U.S. Cl. ...................... 546/114; 514/301
(58) Field of Classification Search .................. 506/114
See application file for complete search history.

(56) References Cited

U.S. PATENT DOCUMENTS

| | | |
|---|---|---|
| 6,320,050 B1 | 11/2001 | Bizzarro et al. |
| 6,353,111 B1 | 3/2002 | Corbett et al. |
| 6,369,232 B1 | 4/2002 | Sidduri |
| 6,384,220 B2 | 5/2002 | Corbett et al. |
| 6,388,071 B2 | 5/2002 | Mahaney |
| 6,388,088 B2 | 5/2002 | Sidduri |
| 6,433,188 B1 | 8/2002 | Corbett et al. |
| 6,441,184 B1 | 8/2002 | Corbett et al. |
| 6,448,399 B1 | 9/2002 | Corbett et al. |
| 6,486,184 B2 | 11/2002 | Kester et al. |
| 6,489,485 B2 | 12/2002 | Bizzarro et al. |
| 6,528,543 B1 | 3/2003 | Bizzarro et al. |
| 6,545,155 B2 | 4/2003 | Corbett et al. |
| 6,583,288 B2 | 6/2003 | Goodnow et al. |
| 6,608,218 B2 | 8/2003 | Kester et al. |
| 6,610,846 B1 | 8/2003 | Bizzarro et al. |
| 6,784,298 B2 | 8/2004 | Goodnow et al. |
| 2001/0039344 A1 | 11/2001 | Bizzarro et al. |
| 2001/0051731 A1 | 12/2001 | Bizzarro et al. |
| 2001/0053851 A1 | 12/2001 | Mahaney |
| 2001/0056191 A1 | 12/2001 | Goodnow et al. |
| 2002/0035266 A1 | 3/2002 | Sidduri |
| 2002/0035267 A1 | 3/2002 | Sidduri |
| 2002/0042512 A1 | 4/2002 | Kester et al. |
| 2002/0082260 A1 | 6/2002 | Guertin |
| 2002/0103241 A1 | 8/2002 | Corbett et al. |
| 2002/0107396 A1 | 8/2002 | Corbett et al. |
| 2002/0198200 A1 | 12/2002 | Kester et al. |
| 2003/0219887 A1 | 11/2003 | Corbett et al. |
| 2003/0225283 A1 | 12/2003 | Corbett et al. |
| 2003/0225286 A1 | 12/2003 | Goodnow et al. |
| 2004/0014968 A1 | 1/2004 | Bizzarro et al. |
| 2004/0067939 A1 | 4/2004 | Corbett |
| 2004/0147748 A1 | 7/2004 | Chen et al. |
| 2004/0186290 A1 | 9/2004 | Fyfe et al. |
| 2007/0265297 A1 | 11/2007 | Bebernitz |
| 2008/0103167 A1 | 5/2008 | Bebernitz |
| 2008/0312256 A1 | 12/2008 | Bebernitz |
| 2008/0318948 A1 | 12/2008 | Bebernitz |

FOREIGN PATENT DOCUMENTS

| | | |
|---|---|---|
| DE | 10259786 A1 | 7/2003 |
| EP | 1 532 980 | 11/2003 |
| GB | 2385328 A | 8/2003 |
| WO | WO 00/58293 | 10/2000 |
| WO | 0144216 A1 | 6/2001 |
| WO | 0183478 A2 | 11/2001 |

(Continued)

OTHER PUBLICATIONS

CA 62:11850, 1965.*
.Colagiuri et al., American Journal of Public Health, Sep. 2006, vol. 96, No. 9, pp. 1562-1569.*
Bruno et al., Expert Opinion Emerging Drugs, (2005), 10(4), pp. 747-771.*
Park, Diabetes Research and Clinical Practice 66S (2004), S33-S35.*
Curtis et al.,The Journal of the American Board of Family Practice, vol. 18, pp. 37-43, (2005).*
Brocklehurst, K. et al., "Stimulation of Hepatocyte Glucose Metabolism by Novel Small Molecule glucokinase Activators", Diabetes, vol. 53, pp. 535-541, Mar. 2004.
Castelhano, A. et al., "Glucokinase-activating Ureas", Bioorg. Med. Chem. Lett., vol. 15, pp. 1501-1504 (2005).

(Continued)

Primary Examiner—Laura L. Stockton
(74) Attorney, Agent, or Firm—Theresa Devlin

(57) ABSTRACT

Compounds of the formula

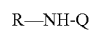

R—NH-Q     (I)

provide pharmacological agents which are glucokinase activators and thus may be employed for the treatment of glucokinase mediated conditions. Accordingly, the compounds of formula (I) may be employed for prevention and treatment of impaired glucose tolerance, Type 2 diabetes and obesity.

8 Claims, No Drawings

FOREIGN PATENT DOCUMENTS

| | | |
|---|---|---|
| WO | WO 01/83465 | 11/2001 |
| WO | WO 01 85706 | 11/2001 |
| WO | WO 01 85707 | 11/2001 |
| WO | WO 02 08209 | 1/2002 |
| WO | WO 02/14312 | 2/2002 |
| WO | 0248106 A2 | 6/2002 |
| WO | WO 02/46173 | 6/2002 |
| WO | WO 03/000262 | 1/2003 |
| WO | 03015774 A1 | 2/2003 |
| WO | WO 03/015774 | 2/2003 |
| WO | WO 03/047626 | 6/2003 |
| WO | WO 03/055482 | 7/2003 |
| WO | 03080585 A1 | 10/2003 |
| WO | 03097824 A1 | 11/2003 |
| WO | WO 03/095438 | 11/2003 |
| WO | 2004002481 A1 | 1/2004 |
| WO | WO 2004/002481 | 1/2004 |
| WO | 2004050645 A1 | 6/2004 |
| WO | WO 2004/052869 | 6/2004 |
| WO | 2004063179 A1 | 7/2004 |
| WO | 2004063194 A1 | 7/2004 |
| WO | 2004072066 A1 | 8/2004 |
| WO | WO 2004/072031 | 8/2004 |
| WO | 2004076420 A1 | 9/2004 |
| WO | 2004081001 A1 | 9/2004 |
| WO | 2005095417 A1 | 10/2005 |
| WO | 2005095418 A1 | 10/2005 |
| WO | 2005103021 A1 | 11/2005 |
| WO | 2006016194 A1 | 2/2006 |
| WO | 2006058923 A1 | 6/2006 |
| WO | 2007041365 A2 | 4/2007 |
| WO | 2007041366 A1 | 4/2007 |

OTHER PUBLICATIONS

Grimsby, J. et al., "Allosteric Activators of Glucokinase: Potential Role in Diabetes Therapy", Science, vol. 301, pp. 370-373, Jul. 18, 2003.

Leighton, B. et al., "Small Molecule glucokinase activators as novel anti-diabetic agents", Chemical Society Transactions, vol. 33, part 2, pp. 371-374 (2005).

McKerrecher, D. et al., "Discovery, synthesis and biological evaluation of novel glucokinase activators", Bioorganic & Medicinal Chemistry Letters, vol. 15, pp. 2103-2106 (2005).

Otaegul, P. et al., "Glucose-Regulated Glucose Uptake by Transplanted Muscle Cells Expressing Glucokinase Counteracts Diabetic Hyperglycemia", Human Gene Therapy, vol. 13, pp. 2125-2133 (Dec. 10, 2002).

Sarabu, et al.: "Targeting glucokinase activation for the treatment of type 2 diabetes—A status review," Current Opinion in Drug Discovery & Development 2005 8(5):631-637.

Guertin et al., "Small Molecule Glucokinase Activators as Glucose Lowering Agents: A New Paradigm for Diabetes Therapy" Current Medicinal Chemistry 13:1839-1843 (2006).

Coope et al., "Predictive blood glucose lowering efficacy by Glucokinase activators in high fat fed female Zucker rats" British Journal of Pharmacology:1-8 (2006).

Printz, et al., "Tweaking the Glucose Sensor: Adjusting Glucokinase Activity with Activator Compounds" Endocrinology 146(9):3693-3695 (Sep. 2005).

Futamura et al., "An Allosteric Activator of Glucokinase Impairs the Interaction of Glucokinase and Glucokinase Regulatory Protein and Regulates Glucose Metabolism," The Journal of Biological Chemistry, Manuscript M605186200 (Oct. 6, 2006).

McKerrecher et al., "Design of a potent, soluble glucokinase activator with excellent in vivo efficacy" Bioorganic & Medicinal Chemistry Letters (2006).

Grimsby, "Discovery and Actions of Glucokinase Activators" Metabolic Diseases World Summit, Jul. 24-25, 2006.

Efanov et al., "A novel glucokinase activator modulates pancreatic islet and hepacyte function" Endocrinology (May 26, 2005).

Matschinsky et al., "The Network of Glucokinase-Expressing Cells in Glucose Homeostasis and the Potential of Glucokinase Activators for Diabetes Therapy" Diabetes 55:1-12 (Jan. 2006).

Office Action mailed in U.S. Patent Application Publication No. 2007-0265297 (U.S. Appl. No. 11/547,227) on Apr. 7, 2009.

Office Action mailed in U.S. Patent Application Publication No. 2008-0103167 (U.S. Appl. No. 11/547,046) on Dec. 19, 2008.

Office Action mailed in U.S. Patent Application Publication No. 2008-0318948 (U.S. Appl. No. 12/088,608) on Sep. 14, 2009.

* cited by examiner

SUBSTITUTED (THIAZOL-2-YL)-AMIDES OR SULFONAMIDES AS GLUCOKINASE ACTIVATORS USEFUL IN THE TREATMENT OF TYPE 2 DIABETES

The present invention relates to thiazole derivatives, pharmaceutical compositions containing them, and to methods of treating glucokinase mediated conditions, in particular, impaired glucose tolerance and Type 2 diabetes, using such compounds.

Accordingly, the present invention provides compounds of the formula (I)

wherein
(i) Q is a

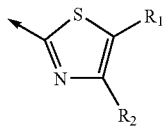

radical in which $R_1$ and $R_2$ are independently hydrogen or halogen; or
Q is a

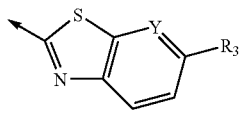

radical in which $R_3$ is hydrogen, halogen, alkyl, cycloalkyl, aryl, alkoxy, cycloalkoxy, aryloxy, alkylthio, cycloalkylthio, arylthio, acyl, sulfonyl, alkylamino, cycloalkylamino, arylamino, acylamino, sulfonamido or alkoxycarbonyl; Y is CH or nitrogen; and
R is a radical of the formula

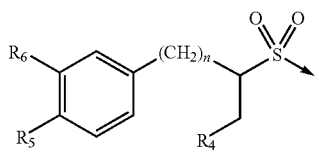

wherein
$R_4$ is $C_{2-4}$alkyl, $C_{3-7}$cycloalkyl or $C_{5-7}$heterocycloalkyl;
$R_5$ and $R_6$ are independently hydrogen, halogen, cyano, $R_7$, —C(O)$R_7$ or —S(O)$_2$$R_7$
wherein
$R_7$ is —(CR$_8$R$_9$)$_m$—W—R$_{10}$ in which
$R_8$ and $R_9$ are independently hydrogen or lower alkyl;
W is a bond, O, S or —NR$_{11}$ in which
$R_{11}$ is hydrogen or lower alkyl;
$R_{10}$ is hydrogen, alkyl, cycloalkyl, aryl or heterocyclyl; or $R_{10}$ and $R_{11}$, combined, are alkylene which together with the nitrogen atom to which they are attached form a 5- to 7-membered ring;
m is zero or an integer from 1 to 5;
n is zero or an integer of 1 or 2;

or an optical isomer thereof; or a pharmaceutically acceptable salt thereof; or
(ii) Q is a

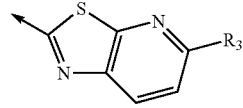

radical in which $R_3$ is hydrogen, halogen, alkyl, cycloalkyl, aryl, alkoxy, cycloalkoxy, aryloxy, alkylthio, cycloalkylthio, arylthio, acyl, sulfonyl, alkylamino, cycloalkylamino, arylamino, acylamino, sulfonamido or alkoxycarbonyl; and
R is a radical of the formula

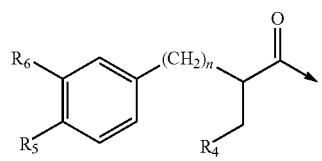

wherein
$R_4$ is $C_{2-4}$alkyl, $C_{3-7}$cycloalkyl or $C_{5-7}$heterocycloalkyl;
$R_5$ and $R_6$ are independently hydrogen, halogen, cyano, $R_7$, —C(O)$R_7$ or —S(O)$_2$$R_7$
wherein
$R_7$ is —(CR$_8$R$_9$)$_m$—W—R$_{10}$ in which
$R_8$ and $R_9$ are independently hydrogen or lower alkyl;
W is a bond, O, S or —NR$_{11}$ in which
$R_{11}$ is hydrogen or lower alkyl;
$R_{10}$ is hydrogen, alkyl, cycloalkyl, aryl or heterocyclyl; or $R_{10}$ and $R_{11}$, combined, are alkylene which together with the nitrogen atom to which they are attached form a 5- to 7-membered ring;
m is zero or an integer from 1 to 5;
n is zero or an integer of 1 or 2;

or an optical isomer thereof; or a pharmaceutically acceptable salt thereof; or
(iii) Q is a

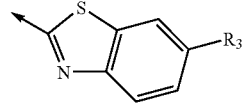

radical in which $R_3$ is hydrogen, halogen, alkyl, cycloalkyl, aryl, alkoxy, cycloalkoxy, aryloxy, alkylthio, cycloalkylthio, arylthio, acyl, sulfonyl, alkylamino, cycloalkylamino, arylamino, acylamino, sulfonamido or alkoxycarbonyl; and R is a radical of the formula

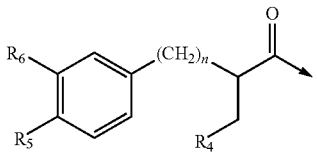

wherein
$R_4$ is $C_{2-4}$alkyl, $C_{3-7}$cycloalkyl or $C_{5-7}$heterocycloalkyl;
$R_5$ and $R_6$ are independently hydrogen, halogen, cyano, $R_7$, —C(O)$R_7$ or —S(O)$_2R_7$
wherein
$R_7$ is —(CR$_8$R$_9$)$_m$—W—$R_{10}$ in which
$R_8$ and $R_9$ are independently hydrogen or lower alkyl;
W is a bond, O, S or —NR$_{11}$ in which
$R_{11}$ is hydrogen or lower alkyl;
$R_{10}$ is hydrogen, alkyl, cycloalkyl, aryl or heterocyclyl; or $R_{10}$ and $R_{11}$, combined, are alkylene which together with the nitrogen atom to which they are attached form a 5- to 7-membered ring;
m is zero or an integer from 1 to 5;
n is zero or an integer of 1 or 2;
provided that: (1) $R_5$ and $R_6$ are not halogen when n is zero; or (2) $R_5$ is not —S(O)$_2R_7$, wherein $R_7$ is —(CR$_8$R$_9$)$_m$—W—$R_{10}$ in which m is zero, W is a bond and $R_{10}$ is $C_{1-3}$alkyl when n is zero;

or an optical isomer thereof; or a pharmaceutically acceptable salt thereof; or
(iv) Q is a

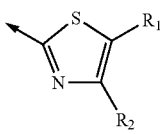

radical, wherein $R_1$ and $R_2$ are independently hydrogen or halogen; and
R is a radical of the formula

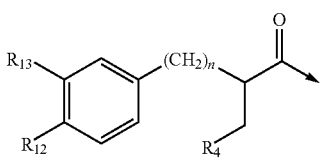

wherein
$R_4$ is $C_{2-4}$alkyl, $C_{3-7}$cycloalkyl or $C_{5-7}$heterocycloalkyl;
$R_{12}$ and $R_{13}$ are independently hydrogen, halogen, cyano, $R_{14}$, —C(O)$R_{14}$, or —S(O)$_2R_{14}$
wherein
$R_{14}$ is —(CR$_8$R$_9$)$_m$—W—$R_{15}$ in which
$R_8$ and $R_9$ are independently hydrogen or lower alkyl;
W is a bond, O, S or —NR$_{11}$ in which
$R_{11}$ is hydrogen or lower alkyl;
$R_{15}$ is cycloalkyl, aryl or heterocyclyl; or $R_{15}$ and $R_{11}$, combined, are alkylene which together with the nitrogen atom to which they are attached form a 5- to 7-membered ring;
m is zero or an integer from 1 to 5;
n is zero or an integer of 1 or 2;
provided that (1) $R_{12}$ and $R_{13}$ both are not hydrogen, halogen, cyano or combinations thereof; (2) $R_{12}$ is not —S(O)$_2R_{14}$, wherein $R_{14}$ is —(CR$_8$R$_9$)$_m$—W—$R_{15}$ in which m is zero and W is a bond when n is zero; (3) $R_{12}$ is not —S(O)$_2R_{14}$, wherein $R_{14}$ is —(CR$_8$R$_9$)$_m$—W—$R_{15}$ in which $R_8$ and $R_9$ are hydrogen, m is 1 and W is a bond when n is zero; (4) $R_{12}$ is not $R_{14}$, wherein $R_{14}$ is —(CR$_8$R$_9$)$_m$—W—$R_{15}$ in which m is zero and W is O when n is zero; or (5) $R_{12}$ is not $R_{14}$, wherein $R_{14}$ is —(CR$_8$R$_9$)$_m$—W—$R_{15}$ in which m is zero and W is a bond when n is zero;

or an optical isomer thereof; or a pharmaceutically acceptable salt thereof.

The compounds of the present invention provide pharmacological agents which are glucokinase activators and, thus, may be employed for the treatment of glucokinase mediated conditions. Accordingly, the compounds of formula (I) may be employed for prevention and treatment of impaired glucose tolerance, Type 2 diabetes and obesity.

Listed below are definitions of various terms used to describe the compounds of the present invention. These definitions apply to the terms as they are used throughout the specification unless they are otherwise limited in specific instances either individually or as part of a larger group, e.g., wherein an attachment point of a certain group is limited to a specific atom within that group, the point of attachment is defined by an arrow at the specific atom.

The term "optionally substituted alkyl" refers to unsubstituted or substituted straight- or branched-chain hydrocarbon groups having 1-20 carbon atoms, preferably 1-10 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more such as 2 or 3 of the following groups: halo, hydroxy, cycloalkyl, alkanoyl, alkoxy, alkyloxyalkoxy, alkanoyloxy, amino, alkylamino, dialkylamino, acylamino, carbamoyl, thiol, alkylthio, alkylthiono, sulfonyl, sulfonamido, sulfamoyl, nitro, cyano, carboxy, alkoxycarbonyl, aryl, alkenyl, alkynyl, aralkoxy, guanidino, heterocyclyl including indolyl, imidazolyl, furyl, thienyl, thiazolyl, pyrrolidyl, pyridyl, pyrimidyl, piperidyl, morpholinyl and the like.

The term "lower alkyl" refers to those optionally substituted alkyl groups as described above having 1-7, preferably 2-4 carbon atoms.

The term "halogen" or "halo" refers to fluorine, chlorine, bromine and iodine.

The term "alkenyl" refers to any of the above alkyl groups having at least two carbon atoms and further containing a carbon to carbon double bond at the point of attachment. Groups having 2-4 carbon atoms are preferred.

The term "alkynyl" refers to any of the above alkyl groups having at least two carbon atoms and further containing a carbon to carbon triple bond at the point of attachment. Groups having 2-4 carbon atoms are preferred.

The term "alkylene" refers to a straight-chain bridge of 4-6 carbon atoms connected by single bonds, e.g., —(CH$_2$)$_x$—, wherein x is 4-6, which may be interrupted with one or more heteroatoms selected from O, S, S(O), S(O)$_2$ or NR, wherein R may be hydrogen, alkyl, cycloalkyl, aryl, acyl, carbamoyl, sulfonyl, sulfamoyl, alkoxycarbonyl, aryloxycarbonyl or aralkoxycarbonyl, or the alkylene may be substituted with one or more substituents selected from alkyl, cycloalkyl, oxo, halogen, hydroxy, carboxy, alkoxy, alkoxycarbonyl and the like.

The term "cycloalkyl" refers to optionally substituted monocyclic, bicyclic or tricyclic hydrocarbon groups of 3-12 carbon atoms, each of which may contain one or more carbon to carbon double bonds, or the cycloalkyl may be substituted by one or more substituents, such as alkyl, halo, oxo, hydroxy, alkoxy, alkanoyl, acylamino, carbamoyl, alkylamino, dialkylamino, thiol, alkylthio, nitro, cyano, carboxy, alkoxycarbonyl, sulfonyl, sulfonamido, sulfamoyl, heterocyclyl and the like.

Exemplary monocyclic hydrocarbon groups include, but are not limited to, cyclopropyl, cyclobutyl, cyclopentyl, cyclopentenyl, cyclohexyl and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

The term "alkoxy" refers to alkyl-O—.
The term "alkanoyl" refers to alkyl-C(O)—.
The term "alkanoyloxy" refers to alkyl-C(O)—O—.
The terms "alkylamino" and "dialkylamino" refer to alkyl-NH— and (alkyl)$_2$N—, respectively,
The term "alkanoylamino" refers to alkyl-C(O)—NH—.
The term "alkylthio" refers to alkyl-S—.
The term "trialkylsilyl" refers to (alkyl)$_3$Si—.
The term "trialkylsilyloxy" refers to (alkyl)$_3$SiO—.
The term "alkylthiono" refers to alkyl-S(O)—.
The term "alkylsulfonyl" refers to alkyl-S(O)$_2$—.
The term "alkoxycarbonyl" refers to alkyl-O—C(O)—.
The term "alkoxycarbonyloxy" refers to alkyl-O—C(O)O—.
The term "carbamoyl" refers to H$_2$NC(O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aralkyl-NHC(O)—, alkyl(aralkyl)-NC(O)— and the like.
The term "sulfamoyl" refers to H$_2$NS(O)$_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.
The term "sulfonamido" refers to alkyl-S(O)$_2$—NH—, aryl-S(O)$_2$NH—, aralkyl-S(O)$_2$—NH—, heteroaryl-S(O)$_2$—NH—, heteroaralkyl-S(O)$_2$—NH—, alkyl-S(O)$_2$N(alkyl)-, aryl-S(O)$_2$N(alkyl)-, aralkyl-S(O)$_2$N(alkyl)-, heteroaryl-S(O)$_2$—N(alkyl)-, heteroaralkyl-S(O)$_2$—N(alkyl)- and the like.
The term "sulfonyl" refers to alkylsulfonyl, arylsulfonyl, heteroarylsulfonyl, aralkylsulfonyl, heteroaralkylsulfonyl and the like.

The term "aryl" refers to monocyclic or bicyclic aromatic hydrocarbon groups having 6-12 carbon atoms in the ring portion, such as phenyl, biphenyl, naphthyl and tetrahydronaphthyl, each of which may optionally be substituted by 1-4 substituents, such as optionally substituted alkyl, trifluoromethyl, cycloalkyl, halo, hydroxy, alkoxy, acyl, alkanoyloxy, aryloxy, optionally substituted amino, thiol, alkylthio, arylthio, nitro, cyano, carboxy, alkoxycarbonyl, carbamoyl, alkylthiono, sulfonyl, sulfonamido, heterocyclyl and the like.

The term "monocyclic aryl" refers to optionally substituted phenyl as described under aryl.

The term "aralkyl" refers to an aryl group bonded directly through an alkyl group, such as benzyl.
The term "aralkanoyl" refers to aralkyl-C(O)—.
The term "aralkylthio" refers to aralkyl-S—.
The term "aralkoxy" refers to an aryl group bonded directly through an alkoxy group.
The term "arylsulfonyl" refers to aryl-S(O)$_2$—.
The term "arylthio" refers to aryl-S—.
The term "aroyl" refers to aryl-C(O)—.
The term "aroyloxy" refers to aryl-C(O)—O—.
The term "aroylamino" refers to aryl-C(O)—NH—.
The term "aryloxycarbonyl" refers to aryl-O—C(O)—.

The term "heterocyclyl" or "heterocyclo" refers to an optionally substituted, fully saturated or unsaturated, aromatic or nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, 1,3-dioxo-1,3-dihydroisoindol-2-yl, dihydroquinazolinyl (such as 3,4-dihydro-4-oxoquinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" includes substituted heterocyclic groups. Substituted heterocyclic groups refer to heterocyclic groups substituted with 1, 2 or 3 substituents selected from the group consisting of the following:
(a) alkyl;
(b) hydroxy (or protected hydroxy);
(c) halo;
(d) oxo, i.e., =O;
(e) optionally substituted amino, alkylamino or dialkylamino;
(f) alkoxy;
(g) cycloalkyl;
(h) carboxy;
(i) heterocyclooxy;
(j) alkoxycarbonyl, such as unsubstituted lower alkoxycarbonyl;

(k) mercapto;
(l) nitro;
(m) cyano;
(n) sulfamoyl or sulfonamido;
(o) aryl;
(p) alkanoyloxy;
(q) aroyloxy;
(r) arylthio;
(s) aryloxy;
(t) alkylthio;
(u) formyl;
(v) carbamoyl;
(w) aralkyl; and
(x) aryl substituted with alkyl, cycloalkyl, alkoxy, hydroxy, amino, acylamino, alkylamino, dialkylamino or halo.

The term "heterocyclooxy" denotes a heterocyclic group bonded through an oxygen bridge.

The term "heterocycloalkyl" refers to nonaromatic heterocyclic groups as described above.

The term "heteroaryl" refers to an aromatic heterocycle, e.g., monocyclic or bicyclic aryl, such as pyrrolyl, pyrazolyl, imidazolyl, triazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl and the like, optionally substituted by, e.g., lower alkyl, lower alkoxy or halo.

The term "heteroarylsulfonyl" refers to heteroaryl-$S(O)_2$—.

The term "heteroaroyl" refers to heteroaryl-C(O)—.

The term "heteroaroylamino" refers to heteroaryl-C(O)NH—.

The term "heteroaralkyl" refers to a heteroaryl group bonded through an alkyl group.

The term "heteroaralkanoyl" refers to heteroaralkyl-C(O)—.

The term "heteroaralkanoylamino" refers to heteroaralkyl-C(O)NH—.

The term "acyl" refers to alkanoyl, aroyl, heteroaroyl, aralkanoyl, heteroaralkanoyl and the like.

The term "acylamino" refers to alkanoylamino, aroylamino, heteroaroylamino, aralkanoylamino, heteroaralkanoylamino and the like.

Pharmaceutically acceptable salts of the compounds of the present invention are salts formed with acids, namely acid addition salts, such as of mineral acids, organic carboxylic acids and organic sulfonic acids, e.g., hydrochloric acid, methanesulfonic acid and maleic acid.

Similarly, pharmaceutically acceptable salts of the compounds of the invention include salts formed with bases, namely cationic salts, such as alkali and alkaline earth metal salts, e.g., sodium, lithium, potassium, calcium and magnesium, as well as ammonium salts, e.g., ammonium, trimethylammonium, diethylammonium and tris(hydroxymethyl)methylammonium salts and salts with amino acids provided an acidic group constitutes part of the structure.

The present invention provides thiazole derivatives of formula (I), pharmaceutical compositions containing them, methods for preparing said compounds, and methods of treating glucokinase mediated conditions by administration of a therapeutically effective amount of a compound of the present invention or a pharmaceutical composition thereof.

In one embodiment, the compounds of formula (I) have the formula

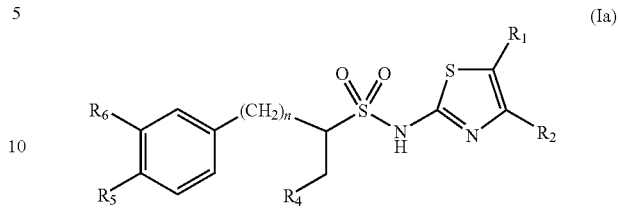

(Ia)

wherein
$R_1$ and $R_2$ are independently hydrogen or halogen;
$R_4$ is $C_{2-4}$alkyl, $C_{3-7}$cycloalkyl or $C_{5-7}$heterocycloalkyl;
$R_5$ and $R_6$ are independently hydrogen, halogen, cyano, $R_7$, —C(O)$R_7$ or —S(O)$_2$$R_7$ wherein
 $R_7$ is —(CR$_8$R$_9$)$_m$—W—R$_{10}$ in which
  $R_8$ and $R_9$ are independently hydrogen or lower alkyl;
  W is a bond, O, S or —NR$_{11}$ in which
   $R_{11}$ is hydrogen or lower alkyl;
  $R_{10}$ is hydrogen, alkyl, cycloalkyl, aryl or heterocyclyl; or $R_{10}$ and $R_{11}$, combined, are alkylene which together with the nitrogen atom to which they are attached form a 5 to 7-membered ring;
 m is zero or an integer from 1 to 5;
n is zero or an integer of 1 or 2;

or an optical isomer thereof; or a pharmaceutically acceptable salt thereof.

Preferred are the compounds of formula (Ia), wherein
$R_4$ is cyclopentyl;
n is zero;

or an optical isomer thereof; or a pharmaceutically acceptable salt thereof.

Other preferred compounds are the compounds of formula (Ia), wherein
$R_4$ is cyclopentyl;
n is zero;
$R_6$ is hydrogen or halogen;
$R_5$ is —S(O)$_2$$R_7$ wherein
 $R_7$ is —(CR$_8$R$_9$)$_m$—W—R$_{10}$ in which
  $R_8$ and $R_9$ are independently hydrogen or lower alkyl;
  W is a bond, O, S or —NR$_{11}$ in which
   $R_{11}$, is hydrogen or lower alkyl preferably hydrogen,
   most preferably W is a bond;
  $R_{10}$ is hydrogen, alkyl, cycloalkyl, aryl or heterocyclyl; or $R_{10}$ and $R_{11}$, combined, are alkylene which together with the nitrogen atom to which they are attached form a 5- to 7-membered ring;
 m is zero or an integer from 1 to 5;

or an optical isomer thereof; or a pharmaceutically acceptable salt thereof.

In another embodiment, the compounds of formula (I) have the formula

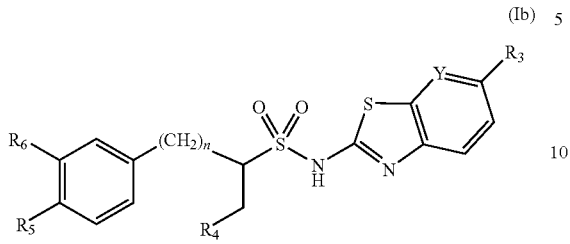

(Ib)

wherein
  $R_3$ is hydrogen, halogen, alkyl, cycloalkyl, aryl, alkoxy, cycloalkoxy, aryloxy, alkylthio, cycloalkylthio, arylthio, acyl, sulfonyl, alkylamino, cycloalkylamino, arylamino, acylamino, sulfonamido or alkoxycarbonyl;
  $R_4$ is $C_{2-4}$alkyl, $C_{3-7}$cycloalkyl or $C_{5-7}$heterocycloalkyl;
  $R_5$ and $R_6$ are independently hydrogen, halogen, cyano, $R_7$, —C(O)$R_7$ or —S(O)$_2R_7$ wherein
    $R_7$ is —(CR$_8$R$_9$)$_m$—W—R$_{10}$ in which
      $R_8$ and $R_9$ are, independently, hydrogen or lower alkyl;
      W is a bond, O, S or —NR$_{11}$ in which R$_{11}$ is hydrogen or lower alkyl;
      $R_{10}$ is hydrogen, alkyl, cycloalkyl, aryl or heterocyclyl; or $R_{10}$ and $R_{11}$, combined, are alkylene which together with the nitrogen atom to which they are attached form a 5 to 7-membered ring;
      m is zero or an integer from 1 to 5;
  Y is CH or nitrogen;
  n is zero or an integer of 1 or 2;

or an optical isomer thereof; or a pharmaceutically acceptable salt thereof.
  Preferred are the compounds of formula (Ib), wherein
  $R_4$ is cyclopentyl;
  n is zero;

or an optical isomer thereof; or a pharmaceutically acceptable salt thereof.
  Other preferred compounds are the compounds of formula (Ib), wherein
  $R_4$ is cyclopentyl;
  n is zero;
  $R_6$ is hydrogen or halogen preferably hydrogen;
  $R_5$ is —S(O)$_2R_7$ wherein
    $R_7$ is —(CR$_8$R$_9$)$_m$—W—R$_{10}$ in which
      $R_8$ and $R_9$ are independently hydrogen or lower alkyl;
      W is a bond, O, S or —NR$_{11}$ in which
        $R_{11}$ is hydrogen or lower alkyl,
        most preferably W is a bond;
      $R_{10}$ is hydrogen, alkyl, cycloalkyl, aryl or heterocyclyl; or $R_{10}$ and $R_{11}$, combined, are alkylene which together with the nitrogen atom to which they are attached form a 5- to 7-membered ring;
      m is zero or an integer from 1 to 5;

or an optical isomer thereof; or a pharmaceutically acceptable salt thereof.

Yet in another embodiment, the compounds of formula (I) have the formula

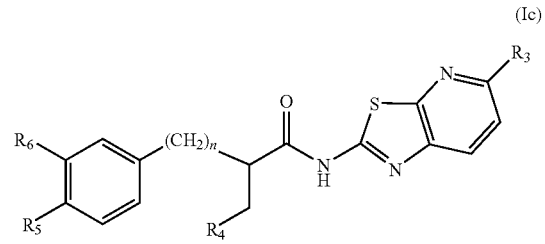

(Ic)

wherein
  $R_3$ is hydrogen, halogen, alkyl, cycloalkyl, aryl, alkoxy, cycloalkoxy, aryloxy, alkylthio, cycloalkylthio, arylthio, acyl, sulfonyl, alkylamino, cycloalkylamino, arylamino, acylamino, sulfonamido or alkoxycarbonyl;
  $R_4$ is $C_{2-4}$alkyl, $C_{3-7}$cycloalkyl or $C_{5-7}$heterocycloalkyl;
  $R_5$ and $R_6$ are independently hydrogen, halogen, cyano, $R_7$, —C(O)$R_7$ or —S(O)$_2R_7$ wherein
    $R_7$ is —(CR$_8$R$_9$)$_m$—W—R$_{10}$ in which
      $R_8$ and $R_9$ are, independently, hydrogen or lower alkyl;
      W is a bond, O, S or —NR$_{11}$ in which
        $R_{11}$ is hydrogen or lower alkyl;
      $R_{10}$ is hydrogen, alkyl, cycloalkyl, aryl or heterocyclyl; or $R_{10}$ and $R_{11}$, combined, are alkylene which together with the nitrogen atom to which they are attached form a 5- to 7-membered ring;
      m is zero or an integer from 1 to 5;
  n is zero or an integer of 1 or 2;

or an optical isomer thereof; or a pharmaceutically acceptable salt thereof.
  Preferred are the compounds of formula (Ic), wherein
  $R_4$ is cyclopentyl;
  n is zero;

or an optical isomer thereof; or a pharmaceutically acceptable salt thereof.
  Other preferred compounds are the compounds of formula (Ic), wherein
  $R_4$ is cyclopentyl;
  n is zero;
  $R_6$ is hydrogen or halogen preferably hydrogen;
  $R_5$ is —S(O)$_2R_7$ wherein
    $R_7$ is —(CR$_8$R$_9$)$_m$—W—R$_{10}$ in which
      $R_8$ and $R_9$ are independently hydrogen or lower alkyl;
      W is a bond, O, S or —NR$_{11}$ in which
        $R_{11}$ is hydrogen or lower alkyl,
        most preferably W is a bond;
      $R_{10}$ is hydrogen, alkyl, cycloalkyl, aryl or heterocyclyl; or $R_{10}$ and $R_{11}$, combined, are alkylene which together with the nitrogen atom to which they are attached form a 5- to 7-membered ring;
      m is zero or an integer from 1 to 5;

or an optical isomer thereof; or a pharmaceutically acceptable salt thereof.
  Other preferred compounds are the preferred compounds of formula (Ic) as described above, wherein $R_3$ is hydrogen or alkoxy.

Yet in another embodiment, the compounds of formula (I) have the formula

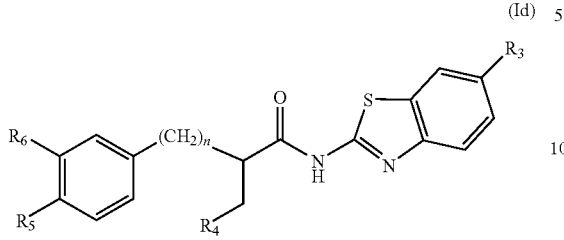

(Id)

wherein
$R_3$ is hydrogen, halogen, alkyl, cycloalkyl, aryl, alkoxy, cycloalkoxy, aryloxy, alkylthio, cycloalkylthio, arylthio, acyl, sulfonyl, alkylamino, cycloalkylamino, arylamino, acylamino, sulfonamido or alkoxycarbonyl;
$R_4$ is $C_{2-4}$alkyl, $C_{3-7}$cycloalkyl or $C_{5-7}$heterocycloalkyl;
$R_5$ and $R_6$ are independently hydrogen, halogen, cyano, $R_7$, —C(O)$R_7$, or —S(O)$_2R_7$ wherein
$R_7$ is —(CR$_8$R$_9$)$_m$—W—R$_{10}$ in which
$R_8$ and $R_9$ are, independently, hydrogen or lower alkyl;
W is a bond, O, S or —NR$_{11}$ in which
$R_{11}$ is hydrogen or lower alkyl;
$R_{10}$ is hydrogen, alkyl, cycloalkyl, aryl or heterocyclyl; or $R_{10}$ and $R_{11}$, combined, are alkylene which together with the nitrogen atom to which they are attached form a 5- to 7-membered ring;
m is zero or an integer from 1 to 5;
n is zero or an integer of 1 or 2;

provided that: (1) $R_5$ and $R_6$ are not halogen when n is zero; or (2) $R_5$ is not —S(O)$_2R_7$, wherein $R_7$ is —(CR$_8$R$_9$)$_m$—W—R$_{10}$ in which m is zero, W is a bond and $R_{10}$ is $C_{1-3}$alkyl when n is zero;

or an optical isomer thereof; or a pharmaceutically acceptable salt thereof.
Preferred are the compounds of formula (Id), wherein
$R_4$ is cyclopentyl;
n is zero;

or an optical isomer thereof; or a pharmaceutically acceptable salt thereof.
Other preferred compounds are the compounds of formula (Id), wherein
$R_4$ is cyclopentyl;
n is zero;
$R_6$ is hydrogen or halogen most preferably hydrogen;
$R_5$ is —S(O)$_2R_7$ wherein
$R_7$ is —(CR$_8$R$_9$)$_m$—W—R$_{10}$ in which
$R_8$ and $R_9$ are independently hydrogen or lower alkyl;
W is a bond, O, S or —NR$_{11}$ in which
$R_{11}$ is hydrogen or lower alkyl,
most preferably W is a bond;
$R_{10}$ is hydrogen, alkyl, cycloalkyl, aryl or heterocyclyl; or $R_{10}$ and $R_{11}$, combined, are alkylene which together with the nitrogen atom to which they are attached form a 5- to 7-membered ring;
m is zero or an integer from 1 to 5;

or an optical isomer thereof; or a pharmaceutically acceptable salt thereof.

Yet in another embodiment, the compounds of formula (I) have the formula

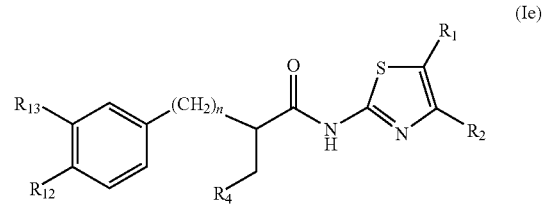

(Ie)

wherein
$R_1$ and $R_2$ are independently hydrogen or halogen;
$R_4$ is $C_{2-4}$alkyl, $C_{3-7}$cycloalkyl or $C_{5-7}$heterocycloalkyl;
$R_{12}$ and $R_{13}$ are independently hydrogen, halogen, cyano, $R_{14}$, —C(O)$R_{14}$, or —S(O)$_2R_{14}$
wherein
$R_{14}$ is —(CR$_8$R$_9$)$_m$—W—R$_{15}$ in which
$R_8$ and $R_9$ are, independently, hydrogen or lower alkyl;
W is a bond, O, S or —NR$_{11}$ in which
$R_{11}$ is hydrogen or lower alkyl;
$R_{15}$ is cycloalkyl, aryl or heterocyclyl; or $R_{15}$ and $R_{11}$, combined, are alkylene which together with the nitrogen atom to which they are attached form a 5- to 7-membered ring;
m is zero or an integer from 1 to 5;
n is zero or an integer of 1 or 2;

provided that: (1) $R_{12}$ and $R_{13}$ both are not hydrogen, halogen, cyano or combinations thereof; (2) $R_{12}$ is not —S(O)$_2R_{14}$ wherein $R_{14}$ is —(CR$_8$R$_9$)$_m$—W—R$_{15}$ in which m is zero and W is a bond when n is zero; (3) $R_{12}$ is not —S(O)$_2R_{14}$, wherein $R_{14}$ is —(CR$_8$R$_9$)$_m$—W—R$_{15}$ in which $R_8$ and $R_9$ are hydrogen, m is 1 and W is a bond when n is zero; (4) $R_{12}$ is not $R_{14}$, wherein $R_{14}$ is —(CR$_8$R$_9$)$_m$—W—R$_{15}$ in which m is zero and W is O when n is zero; or (5) $R_{12}$ is not $R_{14}$, wherein $R_{14}$ is —(CR$_8$R$_9$)$_m$—W—R$_{15}$ in which m is zero and W is a bond when n is zero;

or an optical isomer thereof; or a pharmaceutically acceptable salt thereof.
Preferred are the compounds of formula (Ie), wherein
$R_4$ is cyclopentyl;
n is zero;

or an optical isomer thereof; or a pharmaceutically acceptable salt thereof.
Other preferred compounds are the compounds of formula (Ie), wherein
$R_4$ is cyclopentyl;
n is zero;
$R_6$ is hydrogen or halogen preferably hydrogen;
$R_5$ is —S(O)$_2R_7$ wherein
$R_7$ is —(CR$_8$R$_9$)$_m$—W—R$_{10}$ in which
$R_8$ and $R_9$ are independently hydrogen or lower alkyl;
W is a bond, O, S or —NR$_{11}$ in which
$R_{11}$ is hydrogen or lower alkyl,
most preferably W is a bond;
$R_{10}$ is hydrogen, alkyl, cycloalkyl, aryl or heterocyclyl; or $R_{10}$ and $R_{11}$, combined, are alkylene which together with the nitrogen atom to which they are attached form a 5- to 7-membered ring;
m is zero or an integer from 1 to 5;

or an optical isomer thereof; or a pharmaceutically acceptable salt thereof.

The compounds of the invention depending on the nature of the substituents, may possess one or more asymmetric centers. The resulting diastereoisomers, optical isomers, i.e., enantiomers, and geometric isomers, and mixtures thereof, are encompassed by the instant invention. Preferred are the compounds of the present invention wherein the substituent at the carbon atom adjacent to the amide or sulfonamide group attains the R-configuration.

Compounds of formula (I) may be prepared by coupling amines of the formula $$H_2N-Q' \quad (II),$$

or acid addition salts thereof, wherein Q' represents Q as defined herein above, or Q' is a group convertible to Q, with a compound of the formula $$R'-Lg_1 \quad (III)$$

wherein R' represents R as defined herein above, or R' is a group convertible to R, and $Lg_1$ is a leaving group, e.g., chloride, in the presence of a base such as triethylamine (TEA), diisopropylethylamine (DIEA), N-methylmorpholine (NMM) or pyridine, and an organic solvent, such as dichloromethane (DCM), N,N-dimethylformamide (DMF), acetonotrile or tetrahydrofuran (THF). The reaction may be conducted at an ambient temperature, preferably at a temperature ranging from about −4° C. to about 30° C. Amines of formula (II) and compounds of formula (III) are either commercially available or they may be prepared using methods described herein in the Examples, or modifications thereof, or using methods well-known in the art.

For example, as illustrated in Scheme 1, sulfonyl chlorides of formula (IIIa), wherein $R_4$, $R_5$, $R_6$ and n have meanings as defined herein may be coupled with amines of formula (IIa), wherein $R_1$ and $R_2$ are as defined herein, in the presence of base e.g., pyridine, to afford sulfonamides of formula (IV). Sulfonamides of formula (IV) may then be treated with a base, such as sodium hydride, lithium diisopropylamide (LDA) or lithium bis(trimethylsilyl)amide (LHMDS), preferably LDA, followed by an alkylating agent of formula (V), wherein $R_4$ has a meaning as defined herein, and $Lg_2$ represents a leaving group, such as chloride, bromide or iodide, to afford compounds of formula (Ia). The alkylation step is preferably conducted in a polar organic solvent, such as THF, DMF, N-methylpyrrolidone (NMP) or 1,3-dimethyl-3,4,5,6-tetrahydro-2(1H)-pyrimidinone (DMPU) or in a mixture of solvents thereof.

Scheme 1

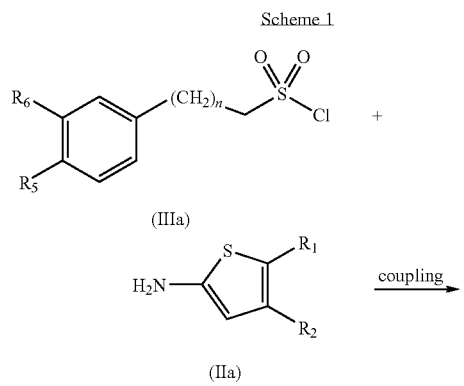

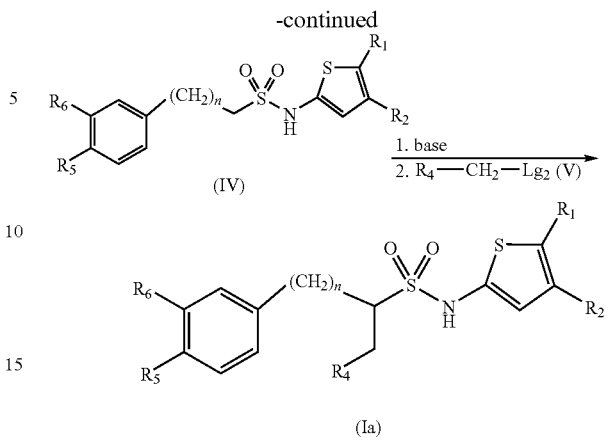

Similarly, as illustrated in Scheme 2, acid chlorides of formula (IIIb), wherein $R_4$, $R_5$, $R_6$ and n have meanings as defined herein, may be coupled with amines of formula (IIa), wherein $R_1$ and $R_2$ are as defined herein, in the presence of base, e.g., pyridine, to afford amides of formula (Ie). Acid chlorides of formula (IIIb) may be prepared as illustrated in Scheme 2, or using methods well-known in the art. For example, esters of formula (VI), wherein $R_{16}$ is lower alkyl, preferably methyl or ethyl, may be treated with a base, such as sodium hydride, LDA or LHMDS, preferably LDA, followed by an alkylating agent of formula (V), wherein $R_4$ has a meaning as defined herein, and $Lg_2$ represents a leaving group, such as chloride, bromide or iodide, to afford compounds of formula (VII). The alkylation step is preferably conducted in a polar organic solvent, such as THF, DMF, NMP or DMPU, or in a mixture of solvents thereof. Compounds of formula (VII) may then be hydrolyzed, e.g., in the presence of an aqueous base such as sodium, lithium or potassium hydroxide and an organic solvent such as THF or lower alcohol, preferably methanol or ethanol. The resulting carboxylic acids may then be treated with a chlorinating agent such as thionyl chloride or oxalyl chloride to afford acid chlorides of formula (IIIb).

Scheme 2

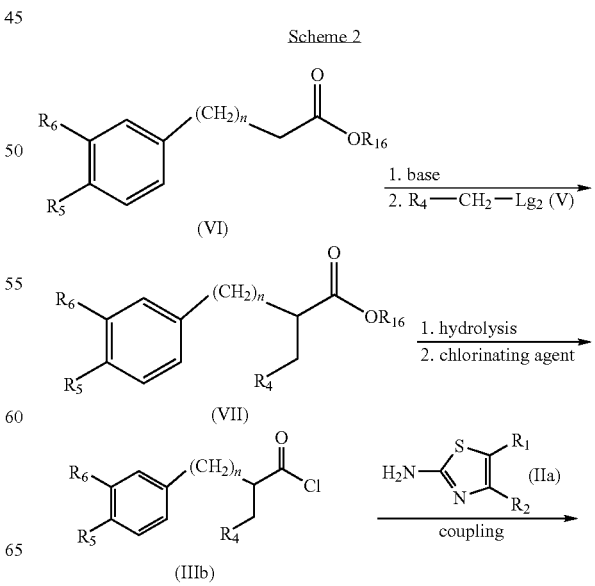

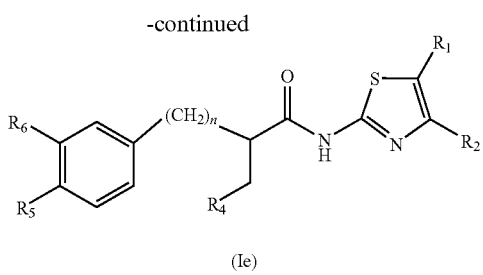

(Ie)

In addition to acid chlorides, other activated derivatives of carboxylic acids may be used, e.g., acid bromides and fluorides, mixed anhydrides, lower alkyl esters, and activated esters thereof, and adducts formed with coupling agents, such as 1-ethyl-3-(dimethylaminopropyl)carbodiimide hydrochloride (EDCl), O-(7-azabenzotriazol-1-yl)-N,N,N',N'-tetramethyluronium hexafluorophosphate (HATU), O-(1,2-dihydro-2-oxo-1-pyridyl)-N,N,N',N'-tetramethyluronium tetrafluoroborate and the like. Mixed anhydrides are preferably such from pivalic acid, or lower alkyl hemiesters of carbonic acids, such as ethyl or isobutyl analogs. Activated esters include, for example, succinimido, phthalimido or 4-nitrophenyl esters. Carboxylic acids may be converted to their activated derivatives using methods described herein, or modifications thereof, or using methods well-known in the art.

The processes described herein above may be conducted under inert atmosphere, preferably under nitrogen atmosphere.

In starting compounds and intermediates which are converted to the compounds of the invention in a manner described herein, functional groups present, such as amino, thiol, carboxyl and hydroxy groups, are optionally protected by conventional protecting groups that are common in preparative organic chemistry. Protected amino, thiol, carboxyl and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, NY (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, room temperature (RT) or elevated temperatures, preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials, intermediates and processes for their manufacture.

Depending on the choice of starting materials and methods, the new compounds may be in the form of one of the possible isomers or mixtures thereof, for example, as substantially pure geometric (cis or trans) isomers, diastereomers, optical isomers (antipodes), racemates or mixtures thereof. The aforesaid possible isomers or mixtures thereof are within the purview of this invention.

Any resulting mixtures of isomers can be separated on the basis of the physicochemical differences of the constituents, into the pure geometric or optical isomers, diastereomers, racemates, for example, by chromatography and/or tractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, the thiazolyl moiety may be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Finally, compounds of the invention are either obtained in the free form, as a salt thereof if salt forming groups are present or as prodrug derivatives thereof.

Compounds of the instant invention which contain acidic groups may be converted into salts with pharmaceutically acceptable bases. Such salts include alkali metal salts, like sodium, lithium and potassium salts; alkaline earth metal salts, like calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids like arginine, lysine and the like. Salts may be formed using conventional methods, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also bemused for purification of the compounds obtained.

Compounds of the invention having basic groups, in particular, the thiazolyl moiety, can be converted into acid addition salts, especially pharmaceutically acceptable salts. These are formed, e.g., with inorganic acids, such as mineral acids, e.g., sulfuric acid, phosphoric or hydrohalic acid, or with organic carboxylic acids, such as ($C_1$-$C_4$)-alkanecarboxylic acids which, e.g., are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, or with organic sulfonic acids, such as ($C_1$-$C_4$)-alkylsulfonic acids, e.g., methanesulfonic acid; or arylsulfonic acids which are unsubstituted or substituted (for example by halogen). Preferred are salts formed with hydrochloric acid, maleic acid and methanesulfonic acid.

Prodrug derivatives of any compound of the invention are derivatives of said compounds which following administration release the parent compound in vivo via some chemical or physiological process, e.g., a prodrug on being brought to the physiological pH or through enzyme action is converted to the parent compound. Exemplary prodrug derivatives are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art.

In view of the close relationship between the free compounds, the prodrug derivatives and the compounds in the form of their salts, whenever a compound is referred to in this context, a prodrug derivative and a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, to activate glucokinase, and for the treatment of conditions associated with glucokinase activity. Such conditions include impaired glucose tolerance, Type 2 diabetes and obesity. The said pharmaceutical compositions comprise a therapeutically effective amount of a pharmacologically active compound of the instant invention, alone or in combination with one or more pharmaceutically acceptable carriers.

The pharmacologically active compounds of the invention are useful in the manufacture of pharmaceutical compositions comprising a therapeutically effective amount thereof in conjunction or admixture with excipients or carriers suitable for either enteral or parenteral application. Preferred are tablets and gelatin capsules comprising the active ingredient together with diluents, e.g., lactose, dextrose, sucrose, mannitol, sorbitol, cellulose and/or glycine; lubricants, e.g., silica, talcum, stearic acid, its magnesium or calcium salt and/or polyethyleneglycol; for tablets also binders, e.g., magnesium aluminum silicate, starch paste, gelatin, tragacanth, methylcellulose, sodium carboxymethylcellulose and/or polyvinylpyrrolidone; and if desired disintegrants, e.g., starches, agar, alginic acid or its sodium salt; or effervescent mixtures; and/or absorbants; colorants; flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and pre-determined rate over a prolonged period of time, and means to secure the device to the skin.

The pharmaceutical formulations contain a therapeutically effective amount of a compound of the invention as defined above, either alone or in a combination with another therapeutic agent, e.g., each at an effective therapeutic dose as reported in the art. Such therapeutic agents include insulin, insulin derivatives and mimetics; insulin secretagogues, such as the sulfonylureas, e.g., Glipizide, glyburide and Amaryl; insulinotropic sulfonylurea receptor ligands, such as meglitinides, e.g., nateglinide and repaglinide; PPARα and/or PPARγ (peroxisome proliferator-activated receptor) ligands such as MCC-555, MK767, L-165041, GW7282 or thiazolidinediones such as rosiglitazone, ploglitazone, troglitazone; insulin sensitizers, such as protein tyrosine phosphatase-1B (PTP-1B) inhibitors such as PTP-112; GSK3 (glycogen synthase kinase-3) inhibitors such as SB-517955, SB-4195052, SB-216763, NN-57-05441, NN-57-05445 or RXR ligands such as GW-0791, AGN-194204; sodium-dependent glucose cotransporter inhibitors, such as T-1095, glycogen phosphorylase A inhibitors, such as BAY R3401; biguanides, such as metformin; alpha-glucosidase inhibitors, such as acarbose; GLP-1 (glucagon like peptide-1), GLP-1 analogs, such as Exendin-4, and GLP-1 mimetics; DPPIV (dipeptidyl peptidase IV) inhibitors such as LAF237; hypolipidemic agents, such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin, fluindostatin and rivastatin, squalene synthase inhibitors or FXR (farnesoid X receptor) and LXR (liver X receptor) ligands, cholestyramine, fibrates, nicotinic acid and aspirin, anti-obesity agents, such as orlistat, anti-hypertensive agents, inotropic agents and hypolipidemic agents, e.g., loop diuretics, such as ethacrynic acid, furosemide and torsemide; angiotensin converting enzyme (ACE) inhibitors, such as benazepril, captopril, enalapril, fosinopril, lisinopril, moexipril, perinodopril, quinapril, ramipril and trandolapril; inhibitors of the Na-K-ATPase membrane pump, such as digoxin; neutralendopeptidase (NEP) inhibitors; ACE/NEP inhibitors, such as omapatrilat, sampatrilat and fasidotril; angiotensin II antagonists, such as candesartan, eprosartan, irbesartan, losartan, telmisartan and valsartan, in particular valsartan; β-adrenergic receptor blockers, such as acebutolol, atenolol, betaxolol, bisoprolol, metoprolol, nadolol, propranolol, sotalol and timolol; inotropic agents, such as digoxin, dobutamine and milrinone; calcium channel blockers, such as amlodipine, bepridil, diltiazem, felodipine, nicardipine, nimodipine, nifedipine, nisoldipine and verapamil. Other specific antidiabetic compounds are described by Patel Mona (Expert Opin Investig Drugs. 2003 April; 12(4):623-33), in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

Thus in an additional aspect the present invention concerns a pharmaceutical composition comprising a therapeutically effective amount of a compound of the invention in combination with one or more pharmaceutically acceptable carriers.

In a further aspect the present invention concerns a pharmaceutical composition comprising a therapeutically effective amount of a compound of the invention in combination with a therapeutically effective amount of another therapeutic agent, preferably selected from antidiabetics, hypolipidemic agents, anti-obesity agents, anti-hypertensive agents or inotropic agents, most preferably from antidiabetics or hypolipidemic agents as described above.

A pharmaceutical composition as described above for use as a medicament.

Use of a pharmaceutical composition or combination as described above for the preparation of a medicament for the treatment of conditions associated with glucokinase activity preferably impaired glucose tolerance, Type 1 or Type 2 diabetes, insulin resistance, dyslipidemia, metabolic syndrome X and obesity preferably Type 2 diabetes, impaired glucose tolerance and obesity.

A pharmaceutical composition as described above for the treatment of conditions associated with glucokinase activity preferably impaired glucose tolerance, Type 1 or Type 2 diabetes, insulin resistance, dyslipidemia, metabolic syndrome X and obesity.

A unit dosage for a mammal of about 50-70 kg may contain between about 1 mg and 1000 mg, advantageously between about 5-500 mg of the active ingredient. The therapeutically effective dosage of a compound of formula (I) is dependent on the species of warm-blooded animal (mammal), the body weight, age and individual condition, on the form of administration and on the compound involved.

The compounds of the present invention are glucokinase activators, and thus may be employed for the treatment of conditions associated with glucokinase activity, as described herein, e.g., impaired glucose tolerance, Type 2 diabetes, insulin resistance, dyslipidemia, metabolic syndrome X and obesity.

Thus, in an additional embodiment, the present invention relates to;

A compound of the invention for use as a medicament

The use of a compound of the invention for the preparation of a pharmaceutical composition for the prevention and/or treatment of conditions associated with glucokinase activity.

A pharmaceutical composition, for use in conditions associated with glucokinase activity comprising a compound of formula I in free form or pharmaceutically acceptable salt form in association with a pharmaceutically acceptable diluent or carrier therefore.

A method for the prevention and/or treatment of conditions associated with glucokinase activity, which comprises administering a therapeutically effective amount of a compound of the invention.

In accordance with the foregoing the present invention provides in a yet further aspect:

A therapeutic combination, e.g. a kit, kit of parts e.g. for use in any method as defined herein, comprising a compound of formula I, in free form or in pharmaceutically acceptable salt form, to be used concomitantly or in sequence with at least one pharmaceutical composition comprising at least another therapeutic agent, preferably selected from antidiabetics, hypolipidemic agents, anti-obesity agents, anti-hypertensive agents or inotropic agents. The kit may comprise instructions for its administration.

A kit of parts comprising
(i) a pharmaceutical composition of the invention, (ii) a pharmaceutical composition comprising a compound selected from an antidiabetic, anti-obesity agent, anti-hypertensive agent, inotropic agent or hypolipidemic agent, or a pharmaceutically acceptable salt thereof, in the form of two separate units of the components (i) to (ii).

A method as defined above comprising co-administration, e.g. concomitantly or in sequence, of a therapeutically effective amount of a compound of formula I in free form or in pharmaceutically acceptable salt form, and a second drug substance, said second drug substance being a antidiabetic, anti-obesity agent, anti-hypertensive agent, inotropic agent or hypolipidemic agent, e.g. as indicated above.

Preferably the compound of the invention is administered to a mammal in need thereof.

Preferably the compound of the invention is used for the treatment of a disease which responds to activation of glucokinase activity.

Preferably the conditions associated with glucokinase activity are selected from impaired glucose tolerance, Type 1 or Type 2 diabetes, insulin resistance, dyslipidemia, metabolic syndrome X and obesity, most preferably Type 2 diabetes, impaired glucose tolerance and obesity.

A method or use according to the invention which comprises administering said compound in combination with a therapeutically effective amount of an antidiabetic agent, anti-obesity agent, anti-hypertensive agent, inotropic agent or hypolipidemic agent.

A method or use according to the invention which comprises administering said compound in the form of a pharmaceutical composition as described herein.

As used throughout the specification and in the claims, the term "treatment" embraces all the different forms or modes of treatment as known to those of the pertinent art and in particular includes preventive, curative, delay of progression and palliative treatment.

The above-cited properties are demonstrable in vitro and in vivo tests using advantageously mammals, e.g., mice, rats, dogs, monkeys or isolated organs, tissues and preparations thereof. Said compounds can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-2}$ molar and $10^{-9}$ molar concentrations. A therapeutically effective amount in vivo may range depending on the route of administration, between about 0.1 mg/kg and 1000 mg/kg, preferably between about 1 mg/kg and 100 mg/kg.

The activity of compounds according to the invention may be assessed by the following methods or methods well-described in the art:

The glucokinase activation in vitro may be determined by measuring the activation of recombinant GST-GK by a compound of the present invention in the absence or the presence of GKRP, a 68,000 Da protein inhibitor of GK. In these assays, formation of glucose-6-phosphate is coupled directly to the formation of thioNADH. GST-GK catalyzes the reaction of glucose and Mg-ATP to produce glucose-6-phosphate and ADP. Glucose-6-phosphate dehydrogenase (G6PDH) reduces thionicotinamide (thioNAD) to thioNADH. The assay measures the formation of NADH at 405 nM.

The basic GK assay components are as follows: 25 mM HEPES (pH 7.1), 25 mM KCl, 2.5 mM $MgCl_2$, 1 mM ATP (Sigma A-5394), 1 mM DTT, 1 mM thioNAD (Sigma T-7375), 80 units/mL G6PDH (Sigma G-5885), 10 mM glucose and 8.7 mg/mL GST-GK (110 nM). For assessing reversal of GK inhibition by GKRP, 20 μM Fructose-1-phosphate (F-6-P) and 25 μg/mL of recombinant GKRP (370 nM) are added to these assay components. F-1-P at 1 μM is used as a control in the GK/GKRP assay. F-1-P reverses inhibition of GST-GK by GKRP.

The assay is done in standard, 96-well, round-bottom plates and the total assay volume is 25 μL. Compounds are serially diluted into 100% DMSO and 0.5 μL of diluted compound in 100% DMSO is added to the assay plate. Assay reagents (24.5 μL) are added using a Zymark robotic platform. Buffer, containing HEPES, $MgCl_2$, KCl, thioNAD, G6PDH, F-6-P, glucose, GKRP and GST-GK, are added (5 μL) using the Zymark 8-channel hand pipet. The reaction is then initiated by adding 19.5 μL of buffer containing HEPES, $MgCl_2$, KCl, DOTT and ATP using the Zymark Reagent Addition Station/Reagent Addition Module. The plates are then delivered via the Zymark XP arm to a Thermomax plate reader and read kinetically over three min at 405 nM at RT. Units are expressed as milli-optical density per minute (mOD/min).

The glucokinase activation in rat hepatocytes may be determined as follows:

Hepatocytes are isolated by collagenase perfusion of the livers of overnight-fasted male Harlen Sprague-Dawley rats (Charles River Laboratories, Raleigh, N.C.) as previously described (see Berry et al., *J. Cell Biol.*, Vol. 43, pp. 506-520 (1969)). The cells are washed three times each with 100 mL of glucose-free Dulbecco's Modified Eagle medium (DMEM, Gibco BRL) containing 5% fetal bovine serum (FBS) and then suspended in glucose-free DMEM/5% FBS. Cells are plated in collagen coated 24-well plates (Becton Dickinson) at a density of $3 \times 10^5$ cells/well in 1 mL of William's Medium E (Sigma) supplemented with 5% FBS, and incubated at 37° C. in 5% $CO_2$/95% air. After cell attachment (~4 h), the medium is replaced with serum-free DMEM containing 5 mM glucose and 10 nM dexamethasone (Sigma), and cells are cultured further for 16-20 h prior to use.

The rate of glucose phosphorylation is determined by the release of $^3H_2O$ from $[2-^3H]$glucose. The medium from the cultured hepatocytes is removed, and the cells are pre-incubated in 150 μL of fresh serum-free DMEM containing 5 mM glucose and compound (1, 10 and 30 μM) or DMSO for 3 h at 37° C. The final concentration of DMSO is 0.2%. The medium is then removed and 150 μL of a fresh mixture of DMEM/5 mM glucose containing compound or DMSO, and 1 μCi of $[2-^3H]$glucose (NEN) is added. As a positive control for stimulation of glucose phosphorylation, cells are pre-incubated in serum-free DMEM/5 mM glucose medium containing DMSO for 3 h and then are incubated for 1 h in labeled glucose medium containing 0.5 mM fructose/DMSO (precursor of F-1-P, AnalaR® from BDH). All conditions are tested in quadruplicate where one well per plate received 200 μL of the appropriate medium plus labeled glucose (instead of 150 μL) of which 50 μL is immediately removed and placed in a 1.2 mL microfuge tube (Costar) containing 10 μL of 1 N HCl. This sample is used as a 0-minute time point for determining background $^3H_2O$ release (exchange values). Following the addition of the labeled glucose media, hepatocytes are incubated at 37° C. on a slow moving rocker for 1 h.

On termination of the incubation, 50 μL of the culture medium is collected into microfuge tubes containing 10 μL of 1 N HCl, and determination of $^3H_2O$. The tubes are left uncapped and each is placed inside a 20 mL glass scintillation vial (Wheaton) containing 1.5 mL of deionized water. The vials are capped tightly and incubated at 37° C. in a dry incubator for 2 days ($^3H_2O$ from the reaction mixture will equilibrate with the water in the vial). A standard curve is generated using $[^3H]H_2O$ (NEN) to correct for exchange. 50 μL aliquots of serial dilutions of the labeled water are added to 10 μL of 1 N HCl and exchange is performed as described for the samples (typically, approximately 90% exchange is observed). The microfuge tubes are then removed from the vials carefully to minimize the removal of any water from the vial and 18 mL of scintillation cocktail (Ready Safe, Beckman Coulter) is then added to each vial. The $^3H$-label recovered from $[2-^3H]$glucose in the water is determined using a Beckman Model LS500 scintillation counter and the counts (minus the 0-time point) are corrected for recovery of $^3H_2O$. The amount of glucose de-tritiated in nanomoles/h per $10^6$ cells is calculated, and the results are expressed as percent increase over the DMSO control.

Our compounds exhibit high affinity, selectivity, improved potency as well as good oral bioavailability, pharmacokinetic profile and safety.

Our compounds are particularly useful for treating diabetes or IGT without a serious risk of hypoglycemia, and have the potential to decrease the risk of cardiovascular diseases in patients especially in individuals with type 2 diabetes or IGT. Thus, our compounds would be appropriate to use for long-term treatments, particularly for use in diabetes, in diabetes prevention such as in IGT patients. Our compounds exhibit a stronger control of the fasting plasma glucose level, postprandial plasma glucose level, serum triglycerides level, haemoglobin A1c level without a serious risk of hypoglycemia or fat mass increase. Furthermore, they exhibit long duration of action, long-term tolerability, safety and lower glycaemic peaks as well as a better daily control of the plasma insulin level. Our compounds have the advantage to augment hepatic glucose metabolism, glucose usage in the liver and glucose-induced insulin secretion from pancreatic islets with a higher efficacy which should provide greater efficacy as a monotherapy.

The following Examples are intended to illustrate the invention and are not to be construed as being limitations thereon. If not mentioned otherwise, all evaporations are performed under reduced pressure, preferably between about 50 mmHg and 100 mmHg. The structure of final products, intermediates and starting materials is confirmed by standard analytical methods, e.g., microanalysis, melting point (m.p.) and spectroscopic characteristics, e.g., MS, IR and NMR. Abbreviations used are those conventional in the art.

EXAMPLE 1

3-Cyclopentyl-2-[4-(2-phenyl-ethanesulfonyl)-phenyl]-N-thiazol-2-yl-propionamide

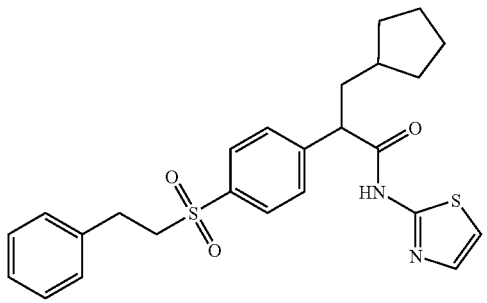

A. 3-Cyclopentyl-2-(4-methanesulfonyl-phenyl)-propionic acid methyl ester

To a solution of diisopropylamine (25 mmol, 3.6 mL) in 24 mL of THF and 7.5 mL of methidathion (DMTP) at −78° C. is added n-BuLi (25 mmol, 10 mL, 2.5 M in hexanes) and the mixture stirred for 15 min. 4-Methylsulfonylphenylacetic acid methyl ester (24 mmol, 5.47 g) in 24 mL of THF and 7.5 mL of DMTP is then added dropwise over 30 min and the reaction is stirred for 90 min further. Cyclopentylmethyliodide (28.9 mmol, 6.08 g) in 10 mL of THF is then added dropwise and the reaction is stirred for 1 h at −78° C. before allowing to warm to RT. After 12 h, the reaction is quenched with water, evaporated and then partitioned between ethyl acetate (EtOAc) and brine, and the organic solution is dried and evaporated to afford an oil. The crude material is chromatographed on silica (eluent: 5%→25% EtOAc in hexanes) to afford 3-cyclopentyl-2-(4-methanesulfonyl-phenyl)-propionic acid methyl ester.

B. 3-Cyclopentyl-2-(4-methanesulfonyl-phenyl)-propionic acid

The title A compound, 3-cyclopentyl-2-(4-methanesulfonyl-phenyl)-propionic acid methyl ester (17.4 mmol, 5.4 g) is saponified under standard conditions using aqueous 1 N aqueous NaOH in methanol (MeOH) with warming to 60° C. in an oil bath. The solvent is removed by evaporation and the aqueous residue is acidified with aqueous 6 N aqueous HCl. The resulting solid is collected by filtration and washed with water and dried under vacuum to afford 3-cyclopentyl-2-(4-methanesulfonyl-phenyl)-propionic acid as a white solid.

C. 3-Cyclopentyl-2-(4-methanesulfonyl-phenyl)-N-thiazol-2-yl-propionamide

The title B compound, 3-cyclopentyl-2-(4-methanesulfonyl-phenyl)-propionic acid (3.44 mmol, 1.02 g) is suspended in thionyl chloride (5 mL) with a catalytic amount of DMF and stirred for 12 h. The mixture is evaporated and then diluted with toluene and re-evaporated to afford an oil which is diluted with 4 mL of DCM and added to 2-aminothiazole (3.8 mmol, 0.4 g) in 10 mL of pyridine at 0° C. and then stirred for 12 h while warming to RT. The reaction mixture is evaporated, diluted with EtOAc and 0.1 N HCl and the organic solution is washed with brine, dried and evaporated to an oil. Chromatography on silica (eluent: 5%→25% EtOAc in hexanes) affords 3-cyclopentyl-2-(4-methanesulfonyl-phenyl)-N-thiazol-2-yl-propionamide: $^1$H NMR δ 11.7 (s, 1H), 7.86 (d, J=8, 2H), 7.55 (d, J=3.5, 1H), 7.53 (d, J=8, 2H), 7.10 (d, J=3.5, 1H), 3.81 (t, J=7.5, 1H), 3.03 (s, 3H), 1.1-2.2 (m, 11H).

D. 3-Cyclopentyl-2-[4-(2-phenyl-ethanesulfonyl)-phenyl]-N-thiazol-2-yl-propionamide The title C compound, 3-cyclopentyl-2-(4-methanesulfonyl-phenyl)-N-thiazol-2-yl-propionamide (0.58 mmol, 220 mg) is dissolved in 15 mL of THF and cooled to −78° C. LHMDS (1.2 mmol, 1.2 mL of 1.0 M solution) is added and the mixture is stirred to 1 h at −78° C. Benzyl bromide (0.6 mmol, 103 mg) is added and the mixture stirred at −78° C. for 2 h further. The reaction mixture is quenched with aqueous saturated ammonium chloride, the solvent is evaporated and the residue is partitioned between EtOAc and brine. The organic solution is dried and evaporated to an oil. Chromatography on silica (eluent: 35% EtOAc in hexanes) affords 3-cyclopentyl-2-[4-(2-phenyl-ethanesulfonyl)-phenyl]-N-thiazol-2-yl-propionamide: $^1$H NMR δ 11.8 (s, 1H), 7.86 (d, J=8, 2H), 7.55 (m, 3H), 7.05-7.32 (m, 6H) 3.8 (t, J=7.5, 1H), 3.33 (m, 2H), 3.05 (m, 2H), 2.29 (m, 1H), 1.0-1.9 (m, 8H); e/z (ES) 469 (M+1, 100%).

EXAMPLE 2

2-Cyclopentyl-1-(4-methanesulfonyl-phenyl)-ethanesulfonic acid thiazol-2-ylamide

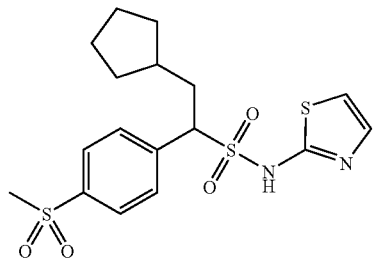

A. (4-Methanesulfonyl-phenyl)-methanesulfonic acid, sodium salt

To a solution of 1-chloromethyl-4-methanesulfonyl-benzene (48.8 mmol, 10 g) in 180 mL of water and 20 mL of DMF is added $Na_2SO_3$ (0.116 mmol, 14.6 g) and the mixture stirred at 40° C. for 12 h. The reaction is evaporated and the resulting solid is triturated with ethanol to afford crude (4-methanesulfonyl-phenyl)-methanesulfonic acid, sodium salt which is used as such in the next step.

B. (4-Methanesulfonyl-phenyl)-methanesulfonyl chloride

To the title A compound, (4-methanesulfonyl-phenyl)-methanesulfonic acid, sodium salt is added $PCl_5$ (10 g) in 200 mL of chloroform and the mixture is stirred for 48 h. The solids are filtered off, the chloroform is removed by evaporation, and the residue is triturated with hexanes, and the solids are collected by filtration to afford (4-methanesulfonyl-phenyl)-methanesulfonyl chloride.

C. C-(4-Methanesulfonyl-phenyl)-N-thiazol-2-yl-methanesulfonamide

To the solution of the title B compound, (4-methanesulfonyl-phenyl)-methanesulfonyl chloride (1.86 mmol, 0.5 g) in 5 mL of pyridine is added 2-aminothiazole (2.5 mmol, 0.25 g) and the mixture is stirred for 48 h. The reaction mixture is quenched with aqueous 1 N HCl and the product is taken up in EtOAc, dried and concentrated to afford C-(4-methanesulfonyl-phenyl)-N-thiazol-2-yl-methanesulfonamide.

D. 2-Cyclopentyl-1-(4-methanesulfonyl-phenyl)-ethanesulfonic acid thiazol-2-ylamide To a solution of diisopropylamine (1.0 mmol, 0.10 g) in 7 mL of THF and 3 mL of DMPU at 0° C. is added n-BuLi (0.61 mL, 2.5 M in hexane) and the reaction mixture is stirred for 15 min, then cooled to −78° C. The title C compound, C-(4-methane-sulfonyl-phenyl)-N-thiazol-2-yl-methanesulfonamide (0.693 mmol, 0.23 g) is added and the reaction mixture is allowed to warm to 0° C. After 1 h, the reaction is recooled to −78° C., cyclopentylmethyliodide (0.72 mmol, 0.15 g) is added and the reaction is allowed to warm to RT over 3 h. The reaction mixture is poured into aqueous 1 N HCl, and the product is taken up in EtOAc, dried and evaporated to afford an orange oil. Chromatography on silica affords 2-cyclopentyl-1-(4-methanesulfonyl-phenyl)-ethanesulfonic acid thiazol-2-ylamide: $^1$H NMR δ 11.6 (br s, 1H), 7.84 (d, J=8, 2H), 7.58 (d, J=8, 2H), 6.67 (d, J=4.5, 1H), 6.39 (d, J=4.5, 1H); 4.27 (m, 1H), 3.03 (s, 3H), 2.04-2.2 (m, 1H), 1.12-1.61 (m, 10H); e/z (ES) 415 (M+1, 100%).

EXAMPLE 3

3-Cyclopentyl-2-(4-methanesulfonyl-phenyl)-N-(5-methoxy-thiazolo[5,4-b]pyridin-2-yl)-propionamide

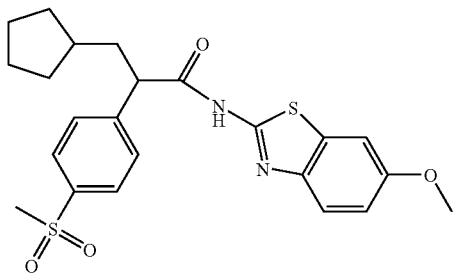

A. 5-Methoxy-thiazolo[5,4-b]pyridin-2-ylamine

A solution of 6-methoxy-pyridin-3-ylamine (40.3 mmol, 5.0 g) in 10 mL of acetic acid is added slowly to a solution of potassium thiocyanate (205 mmol, 20 g) in 100 mL of acetic acid at 0° C. followed by a solution of bromine (48.8 mmol, 2.5 mL) in 5 mL of acetic acid. The reaction is stirred for 2 h at 0° C. and then allowed to warm to RT. The resulting solid is collected by filtration and washed with acetic acid, then partitioned between EtOAc and saturated aqueous NaHCO$_3$. The insoluble material is removed by filtration and the organic layer is dried and evaporated to afford 5-methoxy-thiazolo[5,4-b]pyridin-2-ylamine as a tan solid.

B. 3-Cyclopentyl-2-(4-methanesulfonyl-phenyl)-N-(5-methoxythiazolo[5,4-b]pyridin-2-yl)-propionamide To a solution of the title A compound, 5-methoxy-thiazolo[5,4-b]pyridin-2-ylamine (1.22 mmol, 222 mg) in 3 mL of pyridine at 0° C. is added 3-cyclopentyl-2-(4-methansulfonyl-phenyl)-propionyl chloride (1.02 mmol, prepared as described for the preparation of the title C compound in Example 1). The reaction is allowed to warm to RT over 12 h, then evaporated and the residue is partitioned between MTBE and aqueous 0.1 N HCl. The organic solution is washed with water, saturated aqueous NaHCO$_3$ and brine, dried and evaporated to an oil. Chromatography over silica affords 3-cyclopentyl-2-(4-methanesulfonyl-phenyl)-N-(5-methoxy-thiazolo[5,4-b]pyridin-2-yl)-propionamide; $^1$H NMR δ 9.7 (s, 1H), 7.85 (m, 3H), 7.38 (d, J=8, 2H), 6.83 (d, J=8, 1H), 4.05 (s, 3H), 3.63 (t, J=7.5, 1H); 3.09 (s, 3H), 2.2 (m, 1H), 1.1-1.9 (m, 10H); e/z (ES) 460 (M+1, 100%).

What is claimed is:

1. A compound of the formula

wherein
(i) Q is a

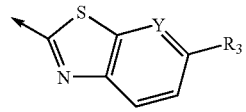

radical in which R$_3$ is an alkoxy; Y is nitrogen; and
R is a radical of the formula

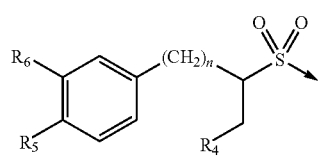

wherein
R$_4$ is C$_{2-4}$alkyl, C$_{3-7}$cycloalkyl or C$_{5-7}$heterocycloalkyl;
R$_5$ and R$_6$ are independently hydrogen, halogen, cyano, R$_7$, —C(O)R$_7$ or —S(O)$_2$R$_7$ wherein
R$_7$ is —(CR$_8$R$_9$)$_m$—W—R$_{10}$ in which
R$_8$ and R$_9$ are independently hydrogen or lower alkyl;
W is a bond,
R$_{10}$ is hydrogen, alkyl, cycloalkyl, aryl or heterocyclyl;
m is zero or an integer from 1 to 5; and
n is zero or an integer of 1 or 2;
or an optical isomer thereof; or a pharmaceutically acceptable salt thereof; or
(ii) Q is a

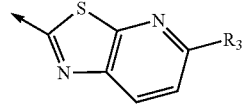

radical in which R$_3$ is alkoxy; and
R is a radical of the formula

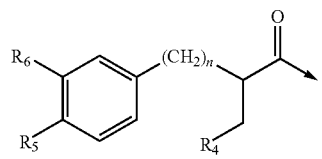

wherein
R$_4$ is C$_{2-4}$alkyl, C$_{3-7}$cycloalkyl or C$_{5-7}$heterocycloalkyl;
R$_5$ and R$_6$ are independently hydrogen, halogen, cyano, R$_7$, —C(O)R$_7$ or —S(O)$_2$R$_7$ wherein
R$_7$ is —(CR$_8$R$_9$)$_m$—W—R$_{10}$ in which
R$_8$ and R$_9$ are independently hydrogen or lower alkyl;
W is a bond;

R$_{10}$ is hydrogen, alkyl, cycloalkyl, aryl or heterocyclyl;
m is zero or an integer from 1 to 5; and
n is zero or an integer of 1 or 2;
or an optical isomer thereof; or a pharmaceutically acceptable salt thereof.

2. A compound according to claim 1 of the formula

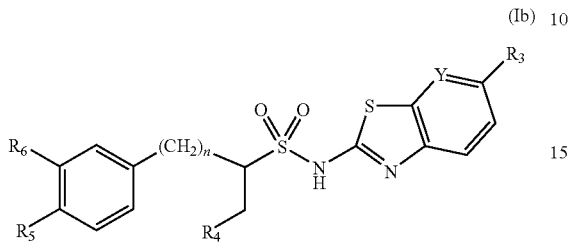

(Ib)

wherein
R$_3$ is alkoxy;
R$_4$ is C$_{2-4}$alkyl, C$_{3-7}$cycloalkyl or C$_{5-7}$heterocycloalkyl;
R$_5$ and R$_6$ are independently hydrogen, halogen, cyano, R$_7$, —C(O)R$_7$ or —S(O)$_2$R$_7$ wherein
R$_7$ is —(CR$_8$R$_9$)$_m$—W—R$_{10}$ in which
R$_8$ and R$_9$ are, independently, hydrogen or lower alkyl;
W is a bond;
R$_{10}$ is hydrogen, alkyl, cycloalkyl, aryl or heterocyclyl;
m is zero or an integer from 1 to 5;
Y is nitrogen;
n is zero or an integer of 1 or 2;
or an optical isomer thereof; or a pharmaceutically acceptable salt thereof.

3. A compound according to claim 2, wherein
R$_4$ is cyclopentyl;
n is zero;
or an optical isomer thereof; or a pharmaceutically acceptable salt thereof.

4. A compound according to claim 1 of the formula

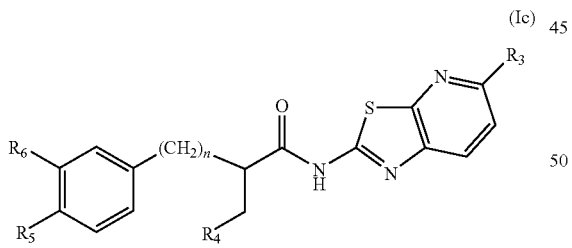

(Ic)

wherein
R$_3$ is alkoxy;
R$_4$ is C$_{2-4}$alkyl, C$_{3-7}$cycloalkyl or C$_{5-7}$heterocycloalkyl;
R$_5$ and R$_6$ are independently hydrogen, halogen, cyano, R$_7$, —C(O)R$_7$ or —S(O)$_2$R$_7$ wherein
R$_7$ is —(CR$_8$R$_9$)$_m$—W—R$_{10}$ in which
R$_8$ and R$_9$ are, independently, hydrogen or lower alkyl;
W is a bond;
R$_{10}$ is hydrogen, alkyl, cycloalkyl, aryl or heterocyclyl;
m is zero or an integer from 1 to 5;
n is zero or an integer of 1 or 2;
or an optical isomer thereof; or a pharmaceutically acceptable salt thereof.

5. A compound according to claim 4, wherein
R$_4$ is cyclopentyl;
n is zero;
or an optical isomer thereof; or a pharmaceutically acceptable salt thereof.

6. A pharmaceutical composition comprising a therapeutically effective amount of a compound of claim 1, or an optical isomer thereof; or a pharmaceutically acceptable salt thereof, in combination with one or more pharmaceutically acceptable carriers.

7. A pharmaceutical composition comprising a therapeutically effective amount of a compound of claim 1, or an optical isomer thereof; or a pharmaceutically acceptable salt thereof, in combination with a pharmaceutically effective amount of insulin, insulin derived mimetic; insulin secretagogue; insulinotropic sulfonylurea receptor ligand; PPAR ligand; insulin sensitizer; biguanide; alpha-glucose inhibitors; GLP-1, GLP-1 analog or mimetic; DPPIV inhibitor; HMG-CoA reductase inhibitor; squaline synthase inhibitor; FXR or LXR ligand; cholestyramine; fibrates; nicotinic acid; or aspirin.

8. A compound according to claim 4, wherein the compound is:

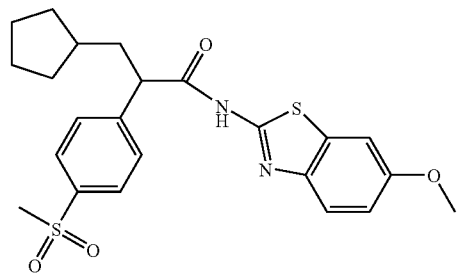

or an optical isomer thereof; or a pharmaceutically acceptable salt thereof.

\* \* \* \* \*